United States Patent
Rappaport et al.

(10) Patent No.: US 6,699,241 B2
(45) Date of Patent: Mar. 2, 2004

(54) WIDE-APERTURE CATHETER-BASED MICROWAVE CARDIAC ABLATION ANTENNA

(75) Inventors: Carey M. Rappaport, Wellesley, MA (US); Paul Wang, Chestnut Hill, MA (US); Zeji Gu, Lexington, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 09/924,927

(22) Filed: Aug. 8, 2001

(65) Prior Publication Data

US 2002/0091427 A1 Jul. 11, 2002

Related U.S. Application Data

(60) Provisional application No. 60/224,964, filed on Aug. 11, 2000.

(51) Int. Cl.$^7$ ............................................... A61B 18/18
(52) U.S. Cl. ..................... 606/33; 607/100; 607/101; 607/156; 606/41
(58) Field of Search ..................... 606/41–50, 33, 606/34; 607/101, 102, 156

(56) References Cited

U.S. PATENT DOCUMENTS

| | | | | |
|---|---|---|---|---|
| 2,043,083 A | * | 6/1936 | Wappler | 607/98 |
| 5,057,106 A | * | 10/1991 | Kasevich et al. | 606/33 |
| 5,413,588 A | * | 5/1995 | Rudie et al. | 607/101 |
| 5,470,352 A | * | 11/1995 | Rappaport | 607/101 |
| 5,693,082 A | * | 12/1997 | Warner et al. | 607/156 |
| 6,002,968 A | * | 12/1999 | Edwards | 607/101 |
| 6,427,089 B1 | * | 7/2002 | Knowlton | 607/101 |

* cited by examiner

*Primary Examiner*—Lee Cohen
*Assistant Examiner*—Aaron Roane
(74) *Attorney, Agent, or Firm*—Weingarten, Schurgin, Gagnebin & Lebovici LLP

(57) ABSTRACT

A catheter-based microwave antenna cardiac ablation applicator has been developed which unlike previously-developed ablation catheters, forms a wide aperture that produces a large heating pattern. The antenna comprises a spiral antenna connected to the center conductor of a coaxial line, and which is insulated from blood and tissue by a non-conductive fluid filled balloon. The antenna can be furled inside a catheter for transluminal guiding. Once in place at the cardiac target, the balloon is inflated, and the coiled spiral antenna is ejected into the inflated balloon. The wide aperture antenna generates a ring-shaped power pattern. The heat generated from this deposited power is conducted through a volume larger than the spiral diameter, ablating diseased tissue. The resultant lesion profile is both wider and deeper than that of either conventionally-used RF catheter-based ablation electrodes, or that of other microwave applicators, and provides greater heating accuracy and controllability.

10 Claims, 16 Drawing Sheets

(4 of 16 Drawing Sheet(s) Filed in Color)

WIDE-APERTURE CATHETER-BASED MICROWAVE CARDIAC ABLATION ANTENNA

CROSS REFERENCE TO RELATED APPLICATIONS

This application claims priority under 35 U.S.C. §119(e) to provisional patent application serial No. 60/224,964 filed Aug. 11, 2000; the disclosure of which is incorporated by reference.

STATEMENT REGARDING FEDERALLY SPONSORED RESEARCH OR DEVELOPMENT

N/A

BACKGROUND OF THE INVENTION

Treating cardiac arrhythmias with electromagnetically-generated heat is becoming widely accepted. Radio Frequency (RF) ablation is an important alternative to pharmacologic treatment, with high success rates in treating a wide range of atrial and ventricular cardiac arrhythmias [1–3]. A similar high success rate has unfortunately not been achieved in patients with ventricular tachycardia [4,5]. Failure to cure ventricular tachycardia associated with coronary artery disease has been attributed to the small lesion size produced with currently available RF ablation catheters. Increasing the power applied to heat tissue at depth often results in excessive temperature at the electrode-tissue interface without the desired enlargement of lesion size. Since desiccation of tissue causes an abrupt rise in impedance and limits energy transfer to the tissue [6], it is believed that the maximum effective depth of the ablated cardiac tissue with the RF method is approximately 0.5 cm. However, in the typical case the myocardial infarction lies much deeper in the ventricular myocardium [7]. In addition, it has been suggested that the zone of slow conduction mediating reentrant ventricular 2 tachycardia may be up to several square centimeters in size [8]. Technologies capable of safely heating such a large volume of tissue, such as those employing microwave energy, may be well suited for ablation of ventricular tachycardia. In contrast to heating by electrical resistance as observed during RF ablation, heating with microwaves is due to a propagating electromagnetic field that raises the energy of the dielectric molecules through which the field passes by both conduction and displacement currents. Thus, in microwave ablation, the initial volume of ablation is a result of direct electromagnetically-induced, dielectric, frictional heating and is unlikely to be limited by local tissue factors or electrode size. This mode of heating lends microwave ablation the potential for a greater depth and larger volume heating than RF ablation and should result in a larger lesion size [9, 10]. Previous research has shown that lesions created by microwave energy increase in size with increased applied power [11].

Microwave catheter-based antenna applicators have been used experimentally for cardiac ablation. These applicators may be grouped into two categories: the monopolar antennas [12, 13] and helical coil antennas [6, 14, 15]. The monopolar antennas are usually one-half tissue wavelength long, designed to radiate in the normal mode to generate a well-defined football-shaped heating pattern along the antenna length. The helical coil antenna applicator is also designed to radiate in the normal mode, perpendicular to the axis of the helix. The helix has been shown to exhibit improved uniformity and localization of heating along the radiating coil portion of the antenna compared to the monopole configuration.

It is desirable, however, to have an illuminating aperture that is as large as possible. The monopole and helix antenna applicators have radiating apertures limited by the diameters of their catheters, and as such must be often be repositioned to create a sufficiently large lesion [16].

BRIEF SUMMARY OF THE INVENTION

A catheter-based microwave antenna cardiac ablation applicator has been developed which unlike previously-developed ablation catheters, forms a wide aperture that produces a large heating pattern. The antenna comprises a spiral antenna connected to the center conductor of a coaxial line, and which is insulated from blood and tissue by a non-conductive fluid filled balloon. The antenna can be furled inside a catheter for transluminal guiding. Once in place at the cardiac target, the balloon is inflated, and the coiled spiral antenna is ejected into the inflated balloon. The wide aperture antenna generates a ring-shaped power pattern. The heat generated from this deposited power is conducted through a volume larger than the spiral diameter, ablating diseased tissue. The resultant lesion profile is both wider and deeper than that of either conventionally-used RF catheter-based ablation electrodes, or that of other microwave applicators, and provides greater heating accuracy and controllability.

Unlike monopole antennas, which radiate normal to their axes, and conventional RF electrodes, which generate radial currents, loop antennas can radiate in either normal or axial modes. Electrically small current loops behave like magnetic dipoles, with electric field strongest in the plane of the loop and polarized circumferentially. However, once the loop circumference approaches one wavelength (in the medium surrounding the loop), the waves it radiates are strongest in the axial direction, with rotating electric field polarized perpendicular to this axis. With proper loop radius adjustment and surrounding medium specification, it is possible to tailor the radiation pattern, creating a ring of deposited power. Thermal conduction then "fills in" the ring, providing a hemi-oblate spheroid lesion shape.

An important aspect of the antenna applicator design is matching of the impedance from applicator to tissue. In practice, an unfurlable spiral formed from the extended center conductor of a coaxial feed line is used instead of a loop. The spiral will be introduced through blood vessels into the heart chamber in a compact, collapsed state, and then ejected from a catheter housing and allowed to reform a spiral shape. It has been determined that the overall length of the center conductor wire governs the antenna impedance. Previous experiments [17] demonstrated that a length of about one tissue wavelength provided the best match to a 50 ohm coaxial cable.

To first order, it is possible to approximately model the spiral antenna as a circular loop. This model gives a sense of the power deposition pattern and thus the heating profiles. For a one wavelength circumference loop, current on one side of the loop will be 180° out of phase and flow in the opposite direction from that on the diametrically opposite side. Thus, these two currents will excite fields which constructively interfere along the axis of the loop and cancel outside the loop. For a loop positioned on a planar tissue surface, this modest focusing yields an enhanced electric field and hence increased power deposition at depth within the tissue. In high water content tissue, one wavelength corresponds to 4.5 cm at 915 MHz [18], which establishes a nominal loop diameter of 1.4 cm.

It has been determined that to produce the desired size lesion of slightly greater than 1 cm diameter and prevent tissue surface overheating, an inner region of low loss, low dielectric constant fluid surrounding the spiral was needed. This physiologically benign fluid, usually air, nitrogen, or a perfluorocarbon blood substitute is contained within a balloon surrounding the loop. An inflation tube is used to fill and drain the fluid. For therapeutic purposes, it is preferable to direct the radiated power directly into the cardiac tissue. Not only does this prevent heating of blood within the heart chamber, it also delivers more of the available power into the heart tissue. Directing the power flow is achieved by asymmetrically positioning the loop in an inflatable balloon, with less fluid in front of the loop than behind it. The loop antenna is specified with radius b placed eccentrically inside the balloon with diameter c, in a plane at a distance l from the center of the balloon. For the spiral within a balloon, the simple model of a single wavelength circumference loop breaks down, and a more sophisticated moment method analysis is required. Repeated experimental and numerical trials concluded that a smaller diameter spiral performs better in the balloon-enclosed environment. The best radius was found to be b=0.5 cm (about 70% of the nominal radius), with balloon radius c=1 cm.

BRIEF DESCRIPTION OF THE SEVERAL VIEWS OF THE DRAWING

The file of this patent contains at east one drawing executed in color. Copies of this patent with color drawing (s) will be provided by the Patent and Trademark Office upon request and payment of the necessary fee.

DETAILED DESCRIPTION OF THE INVENTION

Figure 1:
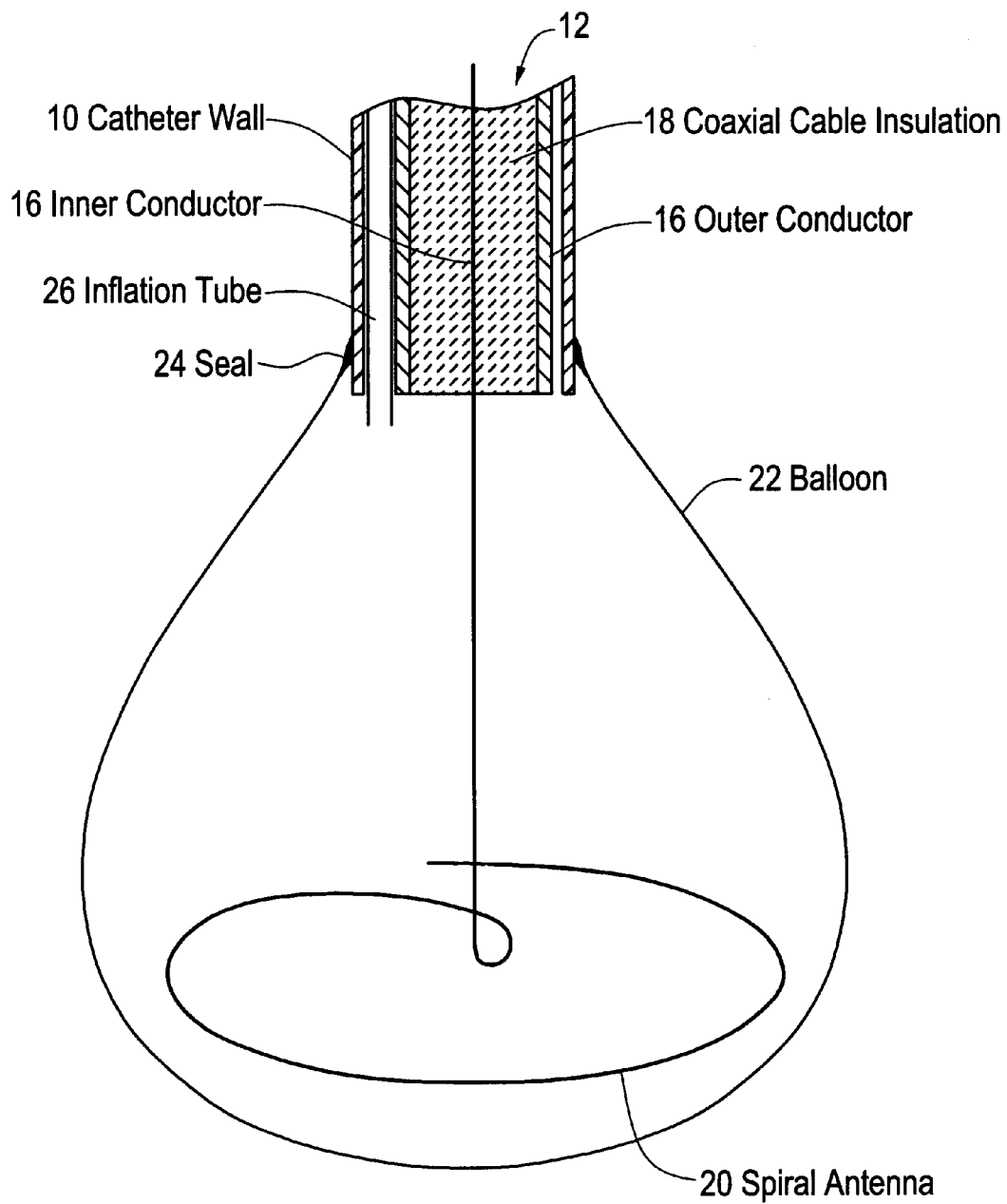
FIG. 1 is a schematic view of the wide aperture microwave ablation catheter and antenna according to the invention showing the structure of the coaxial cable, spiral antenna and the balloon in an unfurled state.
Figure 2:
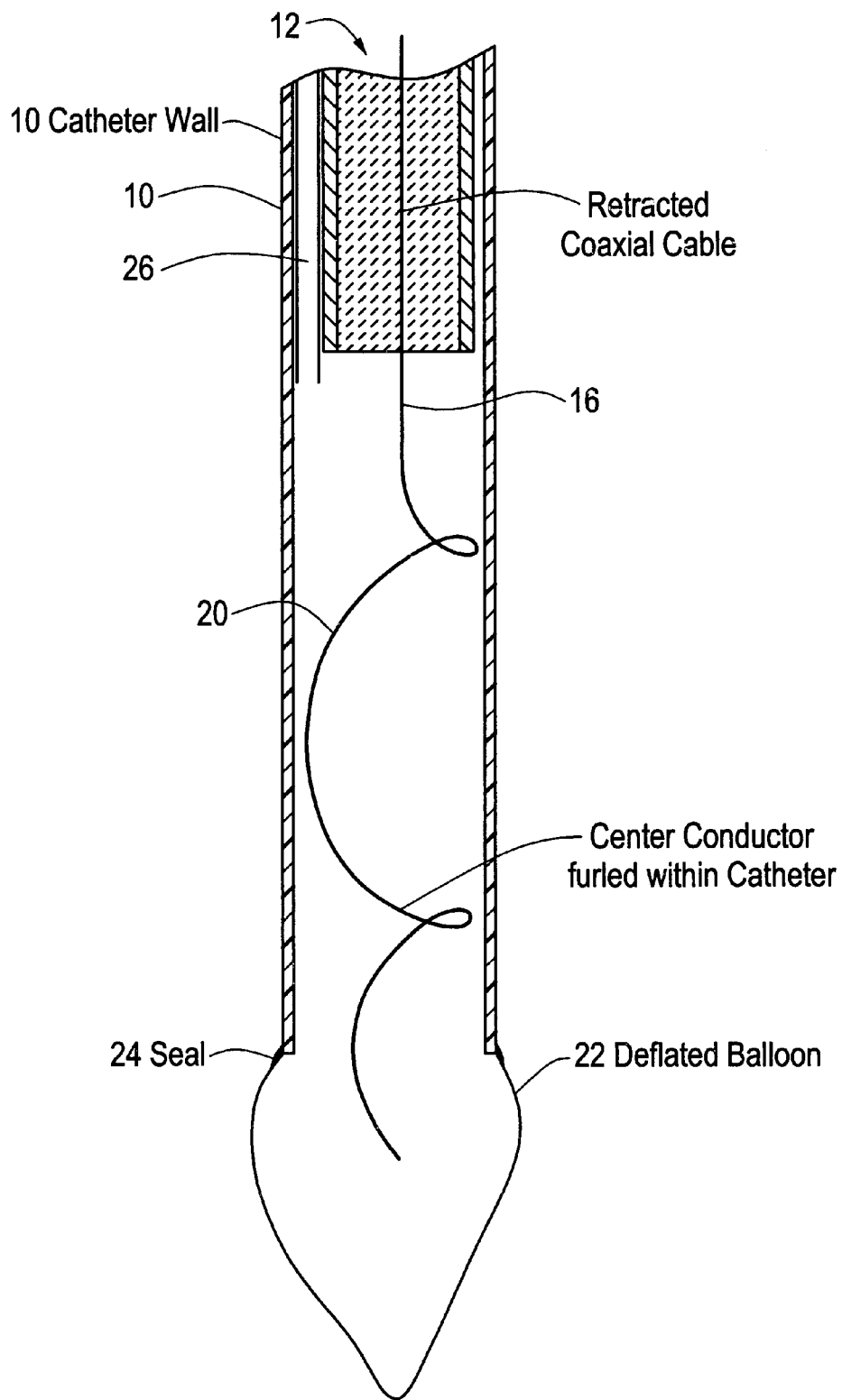
FIG. 2 is a schematic view of the catheter and antenna of FIG. 1 in a furled state.

The cardiac ablation applicator in accordance with the invention is shown in an exemplary embodiment in FIGS. 1 and 2. The applicator is shown in an unfurled state in FIG. 1 and in a furled state in FIG. 2. A catheter 10 which can be of known construction and material, has disposed therein a coaxial cable 12 having an outer conductor 14 and an inner conductor 16 and an electrically insulating material 18 therebetween. The inner conductor 16 extends outwardly from the cable end and is formed into a spiral 20 to provide a spiral antenna. The spiral antenna is disposed within a balloon 22 which is sealed to the catheter wall near an end thereof as shown by seal 24. An inflation tube 26 is disposed within the catheter 10 and has one end terminating at or near the catheter end.

The spiral antenna can have one or more wire turns and can be of a wire size to suit specific embodiments. In the illustrated embodiment the spiral antenna is formed from the inner conductor of the coaxial cable. In an alternative embodiment, the spiral antenna can be formed from a separate wire which is joined to the inner conductor of the coaxial line.

A low loss, low dielectric constant fluid is introduced in the balloon 22 by way of the inflation tube 26 from a suitable source (not shown). A physiologically benign fluid is employed which usually is air, nitrogen or a perfluorocarbon blood substitute. The fluid is also drained from the balloon via the tube 26.

To furl the antenna, the coaxial cable 12 is retracted within catheter 10, which draws the antenna coil into the catheter and which causes a general straightening of the antenna wire within the catheter as illustrated in FIG. 2. The balloon 22 is deflated either before, during or after retraction of the antenna into the catheter. The catheter has the antenna retracted therein, when the catheter is inserted and snaked within a blood vessel to intended position within a heart or other organ or tissue. When in position, the balloon 22 is inflated by introduction of fluid through inflation tube 26, and coaxial cable 12 is pushed through the catheter to a position near the end of the catheter for positioning the antenna 20 outward of the catheter and within the balloon. The antenna wire unfurls when released from the catheter by the inherent springiness of the antenna wire.

The antenna can be implemented in a variety of ways. For example the antenna can be implemented by a metallized path provided on the inside wall of the balloon. The inner end of the metallized spiral terminates in a metallized path which extends to near the balloon opening. The metallized path is joined to the center conductor of the coaxial cable by an extension of the center conductor or by a separate interconnecting wire. In this embodiment the antenna is furled and unfurled during inflation and deflation of the balloon, since the metallized antenna path is sufficiently flexible to accommodate the inflated and deflated balloon configuration. There is no need for longitudinal movement of the coaxial cable within the catheter for this embodiment.

Experiments and Results

To validate the new wide aperture spiral antenna applicator and define the characteristics of microwave heating in myocardial tissue, phantom tests and in vitro tissue tests as well as in vivo living animal tests were performed.

The wide aperture spiral antenna was built from a coaxial RG58 cable, chosen for its high power-handling capability and ease of fabrication of the spiral antenna. The cable jacket and outer conductor were stripped to a length of 4.5 cm, the Teflon insulator was thinned, and then this active segment was curved into a spiral with about 1¼ turns. The coaxial cable was sealed at the antenna end. A tube capable of inflating a balloon was introduced parallel to the coaxial line. The spiral and inflation tube were surrounded by the balloon and firmly sealed with silicon rubber adhesive. The total catheter length was chosen to be 100 cm.

1. Low-Power Phantom Tests

Figure 3:
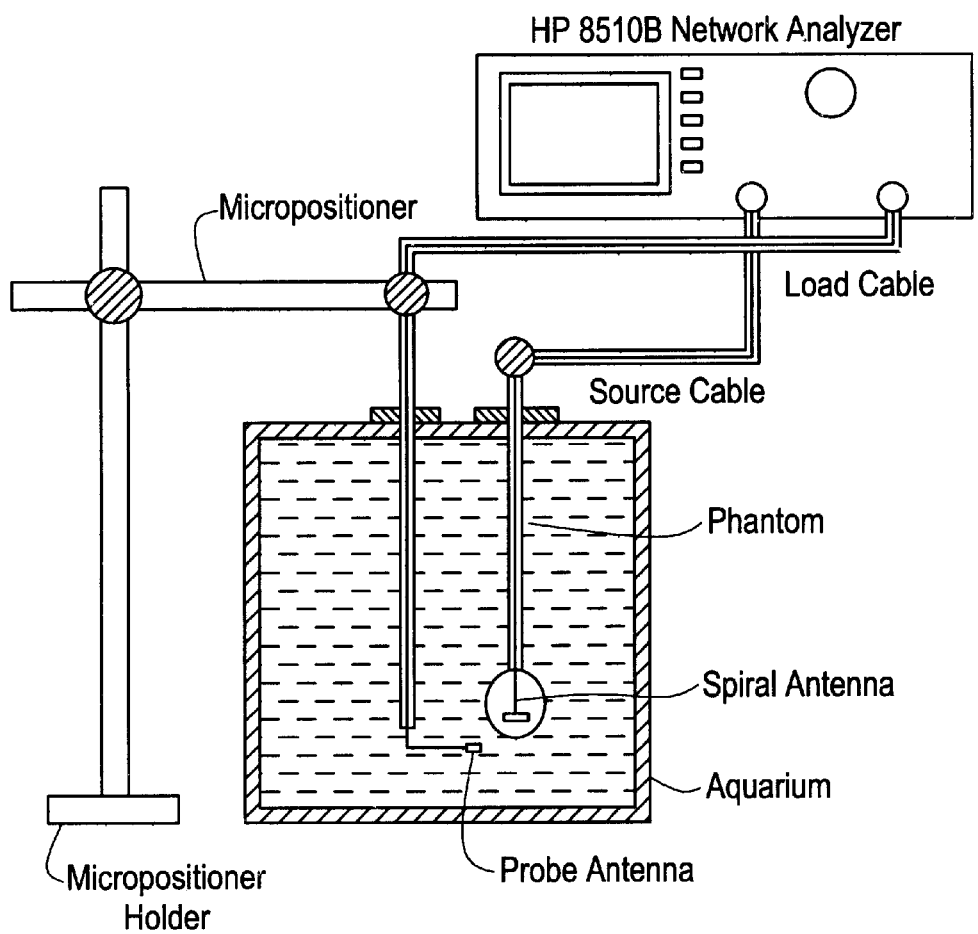
FIG. 3 is a diagrammatic view of the experimental setup for measuring the reflection coefficient S12 and transmission coefficient $S_{21}$ by the spiral antenna embedded in the phantom.

Before the antenna was used for ablation, it was tested in an artificial blood/heart tissue phantom for microwave frequencies in the range from 600 to 1600 MHz using an HP8510B microwave network analyzer, as shown schematically in FIG. 3. The phantom consisted of a saline/sucrose solution, mixed in proportions based on standard recipes, to model the electromagnetic characteristics of high-water-content tissue—such as cardiac tissue and blood—at 915 MHz: the dielectric constant is 51 and electrical conductivity is 1.3 S/m [18]. Measurements of $S_{11}$ were performed with the antenna embedded in the phantom. The antenna penetrated at least 10 cm below the surface to eliminate the dielectric mismatch at the air-phantom interface. The antenna input was mated to the source port of the network analyzer.

Figure 4:
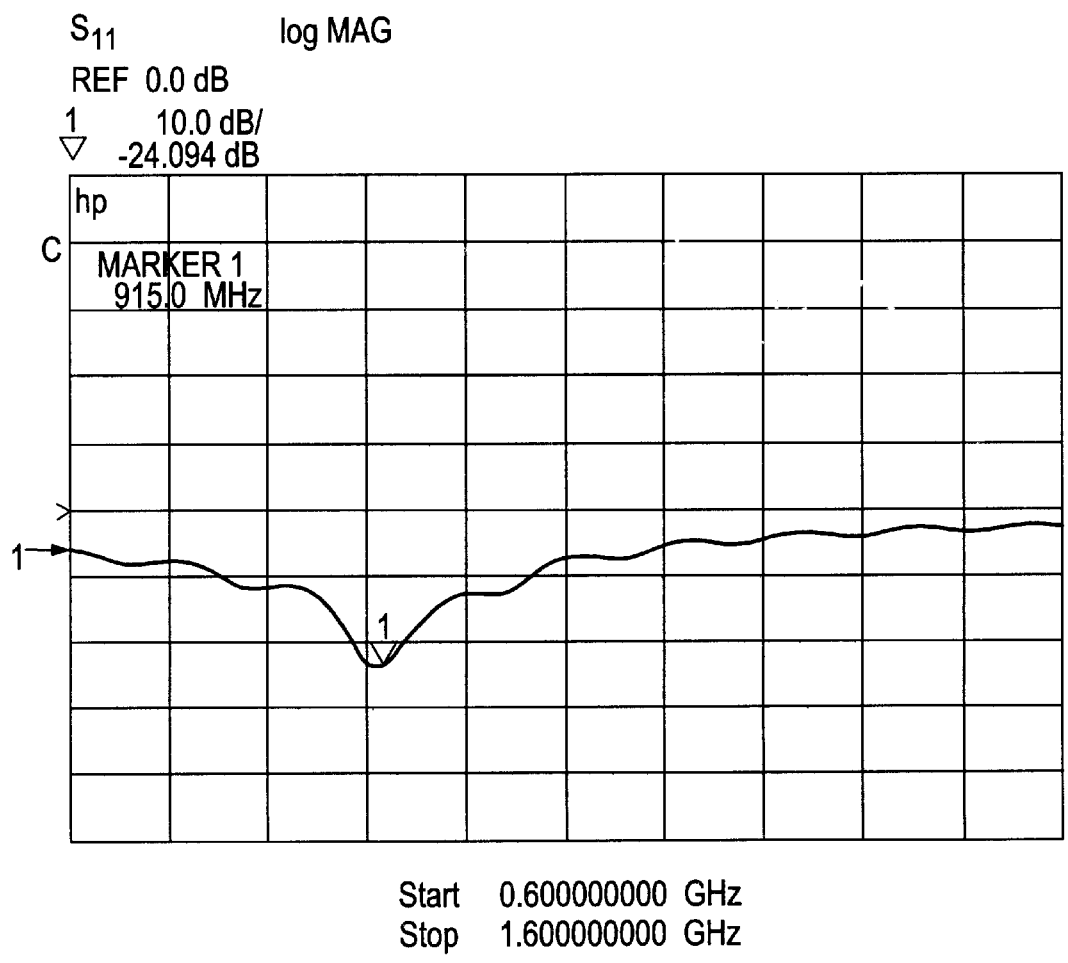
FIG. 4 shows the measured reflection coefficient as a function of frequency for the wide aperture spiral antenna in a heart equivalent liquid phantom, b=0.5 cm, c=1 cm.

FIG. 4 shows the magnitude of the measured reflection coefficient $S_{11}$ of the antenna embedded in the phantom. At the operating frequency of 915 MHz, the value of $S_{11}$ is −21 dB, corresponding to 99.2% of the power supplied being radiated from the antenna and absorbed in the feeding cable. It can thus be concluded that the antenna couples quite well to the biological tissue at 915 MHz.

The transmitted power deposition was measured by using a simple short monopole probe antenna, which sampled the electric field at various locations within the phantom. An inherent and unavoidable limitation of this procedure is that the probe antenna must be very small for high-resolution measurements, but in being so small, it couples poorly to the phantom. Field readings are therefore relative rather than absolute. The probe antenna consists of a coaxial cable with 10 mm of the center conductor extend beyond the outer conductor. The probe can only measure the phase and amplitude of a single polarization of electric field. The squared magnitudes of all electric field polarizations are summed to determine the relative deposited power pattern in the phantom. The spiral antenna and the monopole probe are modeled as a two-port network. According to two-port network theory, the $S_{11}$ measurement gives the ratio of power reflected back from the antenna, and hence gives a measure of how well the antenna radiates power into phantom, while $S_{21}$ represents how well the power is transferred between the two antennas through the phantom.

Figure 5:
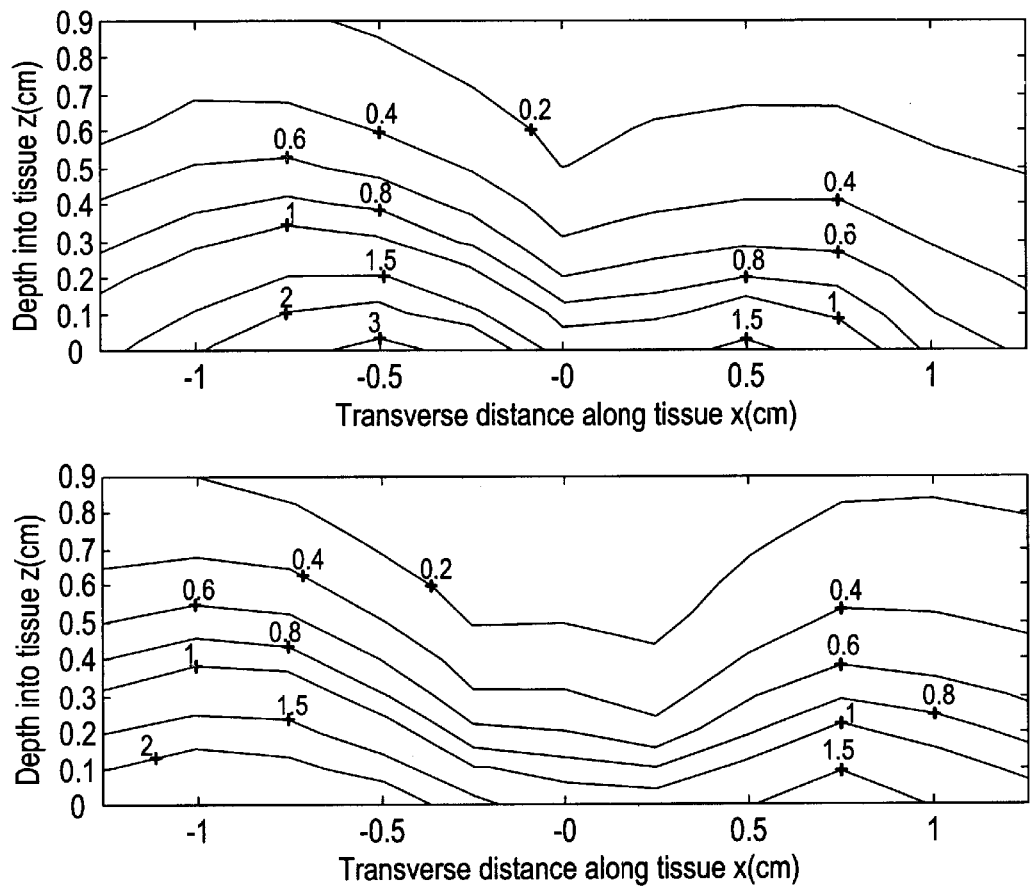
FIG. 5 shows the measured relative deposition power contour plot for spiral antenna asymmetrically surrounded by insulator-filled balloon immersed in phantom, on a) x-z plane and b) y-z plane, b=0.5 cm, c=1 cm. Loop shift distance l/c=0.87. $S_{11}$=−21 dB.

FIG. 5 shows the measured power deposition contours given by squaring the magnitude of $S_{21}$. For the purpose of these plots, the spiral is oriented so that its axis is facing the forward z-direction. FIG. 4a gives the pattern in the x-z plane, which includes the feed line, along the negative x-direction, while FIG. 4b shows the pattern in the y-z plane.

Figure 6:
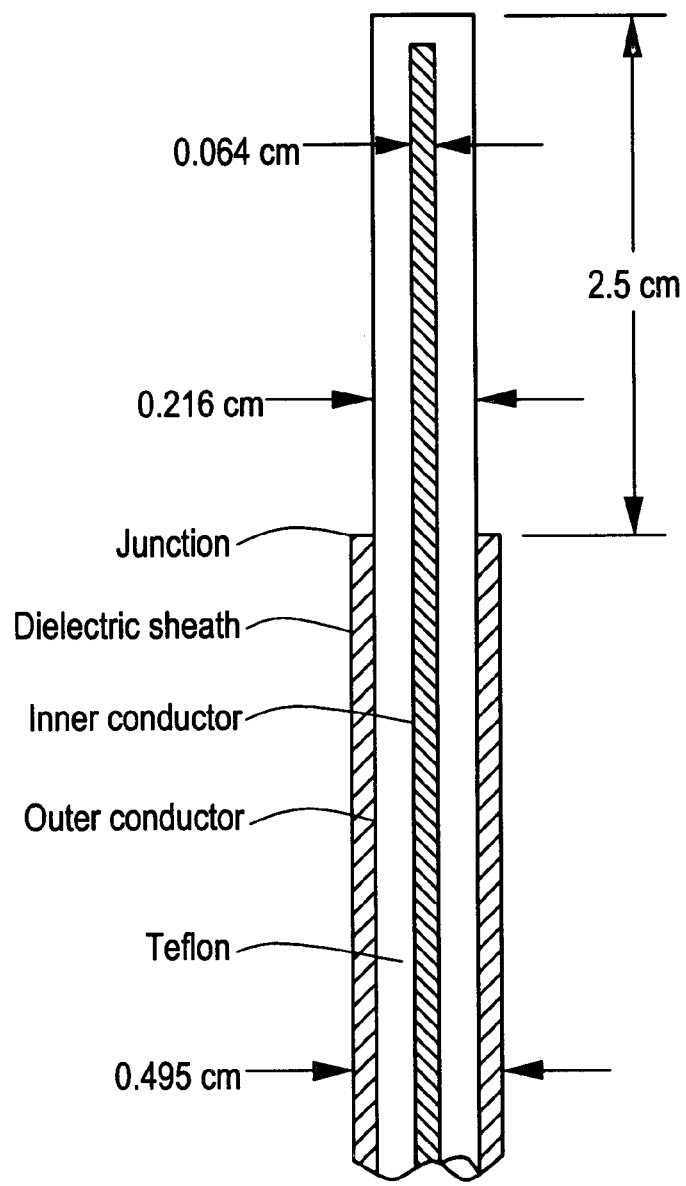
FIG. 6 is a schematic view of a prior art bare monopole microwave antenna, used as an experimental reference.
Figure 7:
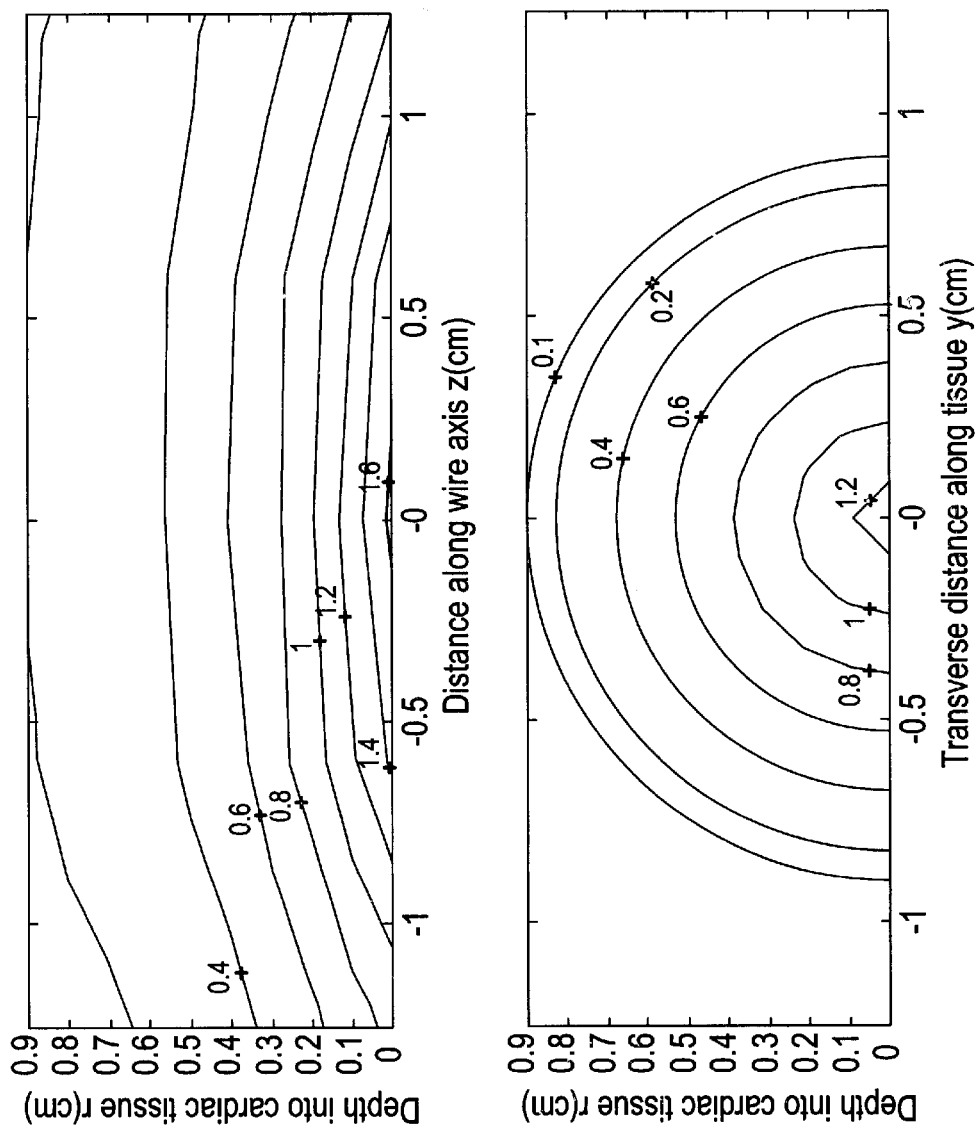
FIG. 7 shows the measured deposition power contour plot for bare monopole antenna immersed in phantom, with length 2.5 cm, on a) z-ρ plane and b) y-ρ plane.

The above results can be compared with those obtained with a simple monopole antenna. A monopole with geometry shown in FIG. 6 was fabricated and measured in the same phantom set-up used previously. The center conductor, pointing in the z-direction parallel and against the tissue surface, extends 2.5 cm, or slightly more than one-half a tissue wavelength. Contour plots for the resulting deposited power patterns are shown in FIG. 7. FIG. 7a shows the power pattern in the z-ρ plane, where the ρ-direction points into the tissue, while FIG. 7b gives the circularly symmetric pattern in the plane perpendicular to the monopole axis.

Comparing the measured relative power deposition patterns for the spiral and monopole antennas indicates the superiority of the former in heating tissue to form well-defined lesions. Whereas the monopole pattern is widely spread along the 2.5 cm wire length, it is narrow in the transverse direction perpendicular to the wire, and power levels fall off relatively quickly with depth into the tissue. The spiral antenna on the other hand deposits more of its power in a ring near the axis of the spiral. The spiral antenna pattern is more nearly circular and is deeper than the monopole antenna pattern.

2. In vitro Tissue Tests

Microwave heating was tested using a custom-built 915 MHz power source with output power level adjustable from 0.001 to 330 W and duration adjustable from 1 s to 99 min. Forward and backward power were monitored throughout the course of each heating experiment. The transmitted power was set to three levels for testing (50, 100 and 150 W), the duration was set at 60 s, and the forward and reflected power was recorded in each case. The antenna was positioned with the antenna axis perpendicular to the surface of the medium to be heated. A fulcrum balanced the weight of the antenna and assured constant tissue pressure. All in vitro and in vivo temperature measurements were performed with the fluoroptic thermometry system (Luxtron model 790, measurement range, −200° C. to 450° C., accuracy ±0.1° C. Luxtron Corp., Santa Clara, Calif.). Prior to each application, 10 cc. of room air inflated the balloon surrounding the spiral antenna. During each application of microwave energy, the power and fluoroptic temperature probes were continuously monitored and recorded.

Figure 8:
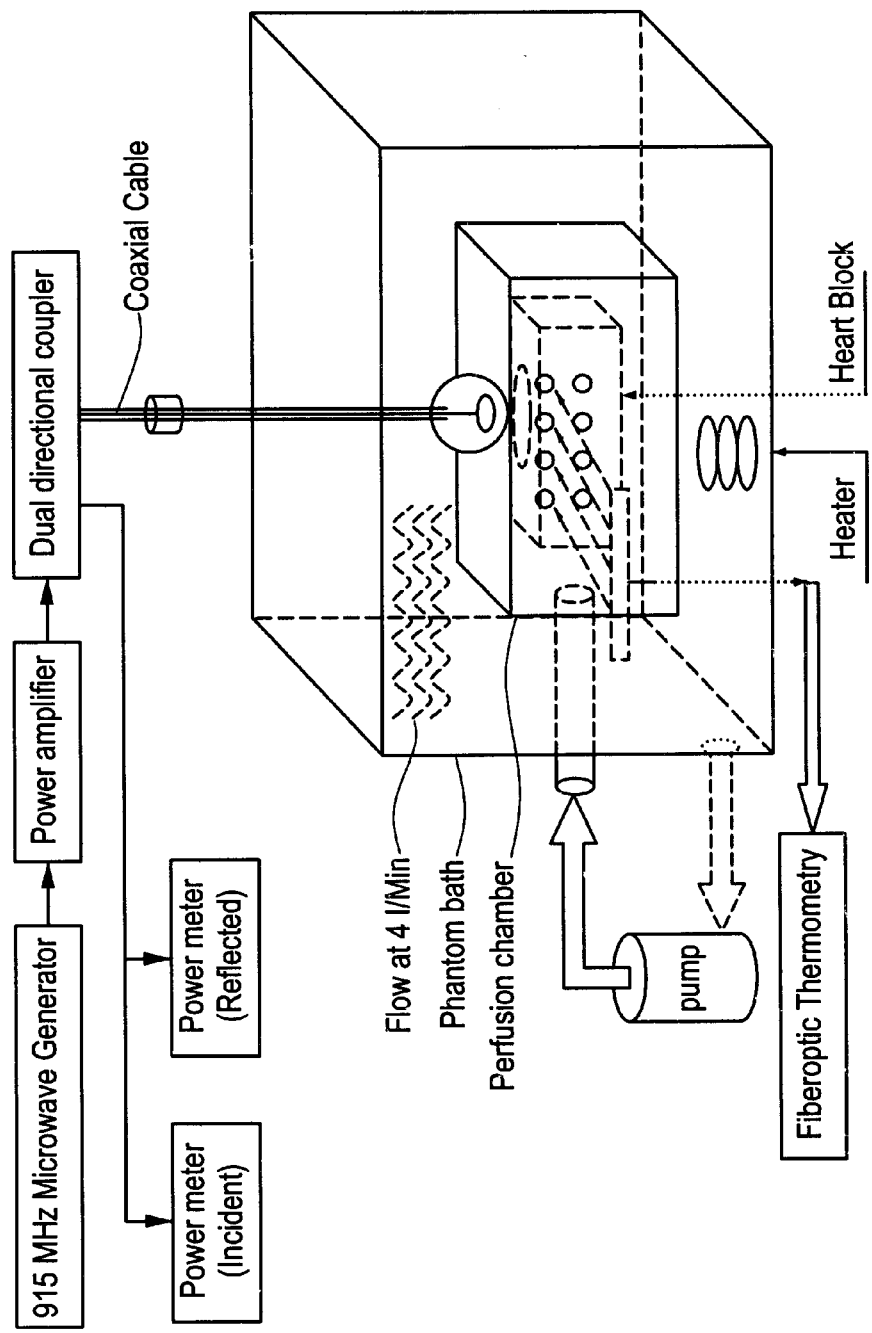
FIG. 8 is a diagram of the perfused pig heart model for evaluation of cardiac ablation catheter.

In vitro experiments were performed in isolated perfused pig hearts to identify how much power would be required to effectively ablate myocardial tissue and to demonstrate the time course of temperature rise and lesion growth during microwave ablation. FIG. 8 shows the experimental setup. We first created a perfused pig heart model to simulate the endocardial environment present in catherter ablation. The model consisted of a sectioned pig heart block suspended in a 4×3×2 cm polystyrene chamber. A perfusion pump controlled flow across the surface of each heart block, simulating blood flow. Four temperature sensors were inserted into each heart block, spaced 5 mm apart.

For each experiment, power was applied for 60 s. The temperature was recorded, the phantom was allowed to cool down for several minutes, the four sensors were withdrawn, the pig heart block was replaced, and the thermometry system was recalibrated. Once the phantom returned to equilibrium within 0.5° C. of initial conditions, the procedure was repeated. Ten tests were performed under identical treatment conditions in order to average unavoidable uncertainties in output power, heating time, and position of the antenna, catheters and temperature probes. These were repeated for each power level.

Once a lesion is created, the effects are clearly irreversible, and new unexposed tissue must be used for testing. However, in contrast to RF ablation, there was no noticeable input impedance change, nor heating rate change due to the lesion formation. Reflected power remained nominal in all experiments for all power levels. This is partly due to lack of tissue charring, but also due to the microwave power deposition mechanism which relies less on material conduction characteristics.

3. In vivo Tests on Pig Thigh Muscle Model

Figure 9:
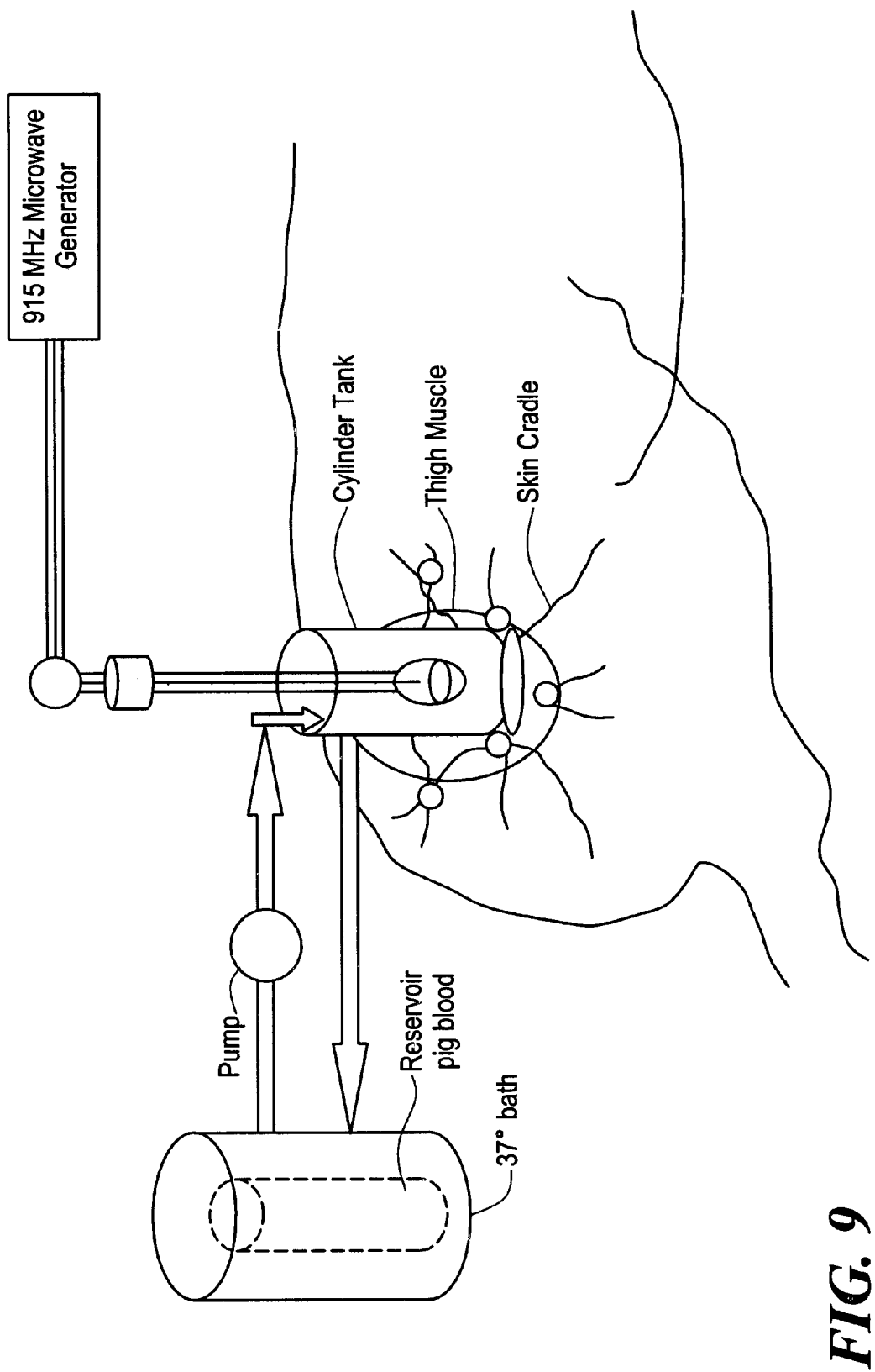
FIG. 9 is a schematic of the thigh muscle model.

The experimental setup for the in vitro tests on thigh muscle model is shown in FIG. 9. The methods employed for the wide-aperture spiral antenna were the same used by Nakagawa [19] for RF electrode tests. These studies were performed to accumulate sufficiently detailed temperature data and compare the tissue temperature at the border zone of irreversible tissue injury.

Five male pigs weighing between 77–89 kg were studied. As tested in the in vitro experiment, the catheter was positioned perpendicular to the thigh muscle, and held in contact with exposed thigh muscle at a constant pressure by use of a custom balance. Tissue temperature was measured with the same fluoroptic probes as used in in vitro tests. Two thermal sensor probes were bundled together with shrink tubing. One sensor tip extended 3 mm from the end of the shrink tubing, and the other sensor tip extended 6.0 mm. The sensor probes were inserted into the muscle (3.0 mm and 6.0 mm from the surface) directly adjacent to the edge of the balloon-tissue interface. An additional fluoroptic temperature probe was attached at the center of the balloon-tissue interface.

Eight to ten applications of microwave energy were delivered to separate sites on the right thigh muscle. The skin incision was closed, the pig was turned onto its right side, and eight to ten applications of microwave energy were delivered at separate sites on the left thigh muscle. Microwave energy was delivered for 60 seconds using one of three power levels: 50, 100, or 150 W. Finally, the lesion was stained and its volume was determined by assuming it had an oblate spheroidal shape with volume given by:

$$V=[4/3\pi A^2 C]/2$$

where A and C represent the surface radius and the depth of the volume, respectively. For 60s heating with 50, 100 and 150 W input power, the resulting lesion volumes were 260, 1200, and 1900 mm$^3$, respectively. The relationship is not linear because the power deposition dependence is not linear with volume, and lesions created by heating tissue to above a particular temperature threshold do not have uniform temperature throughout.

Figure 10A:
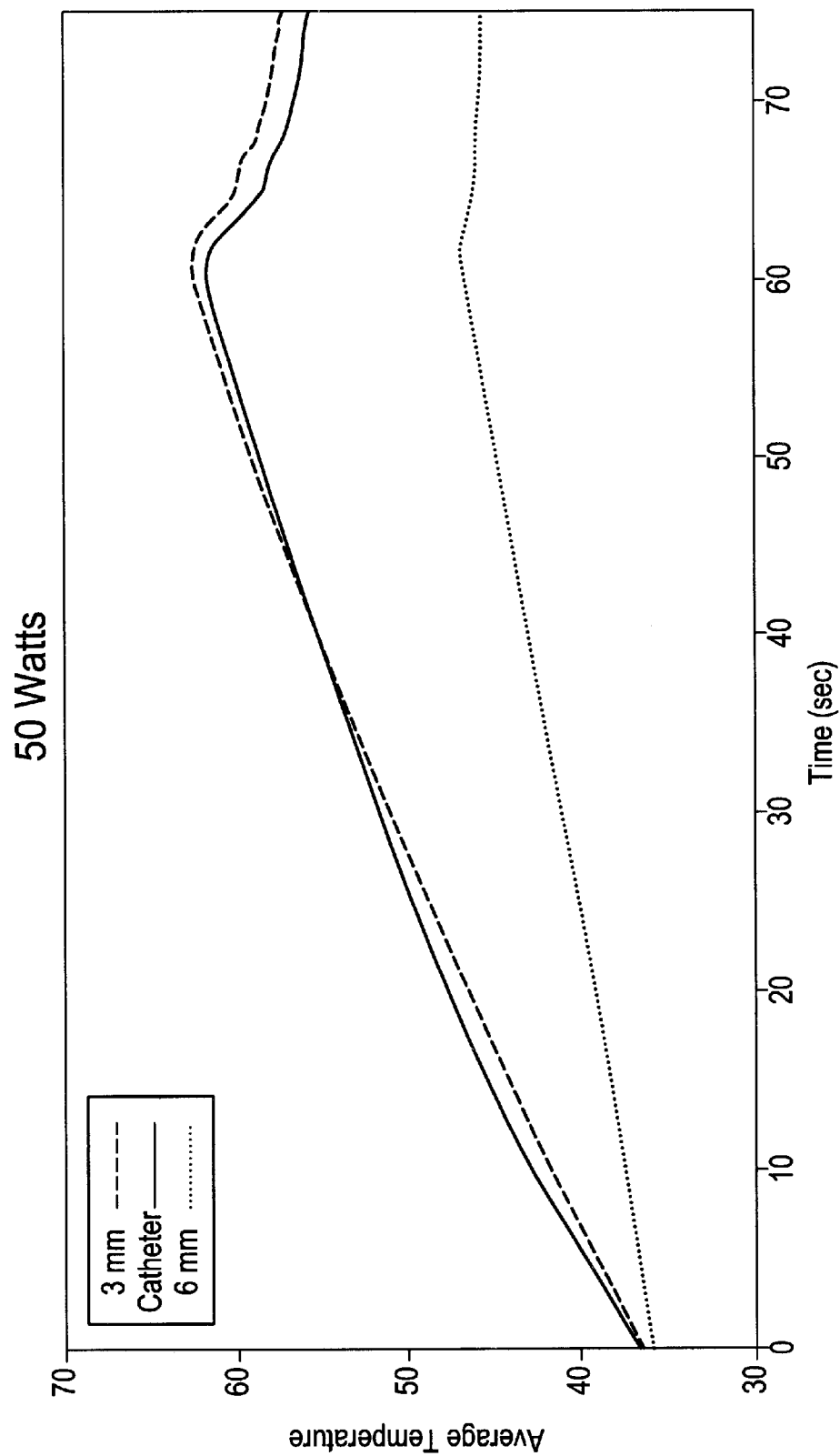
FIG. 10 are curves showing the time course of lesion formation in vivo with various applied powers for 60 second microwave ablation.
Figure 10B:
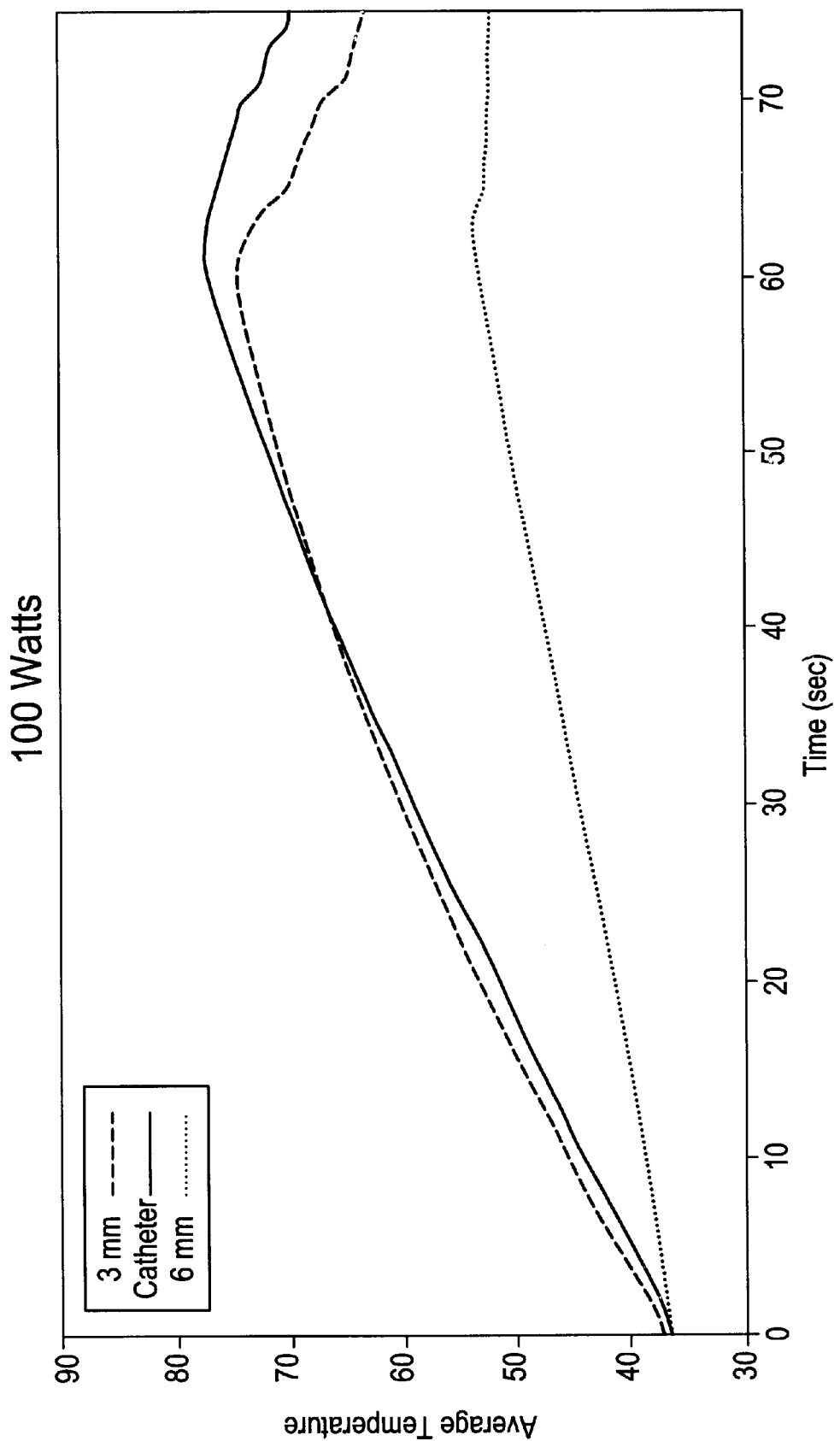
Figure 10C:
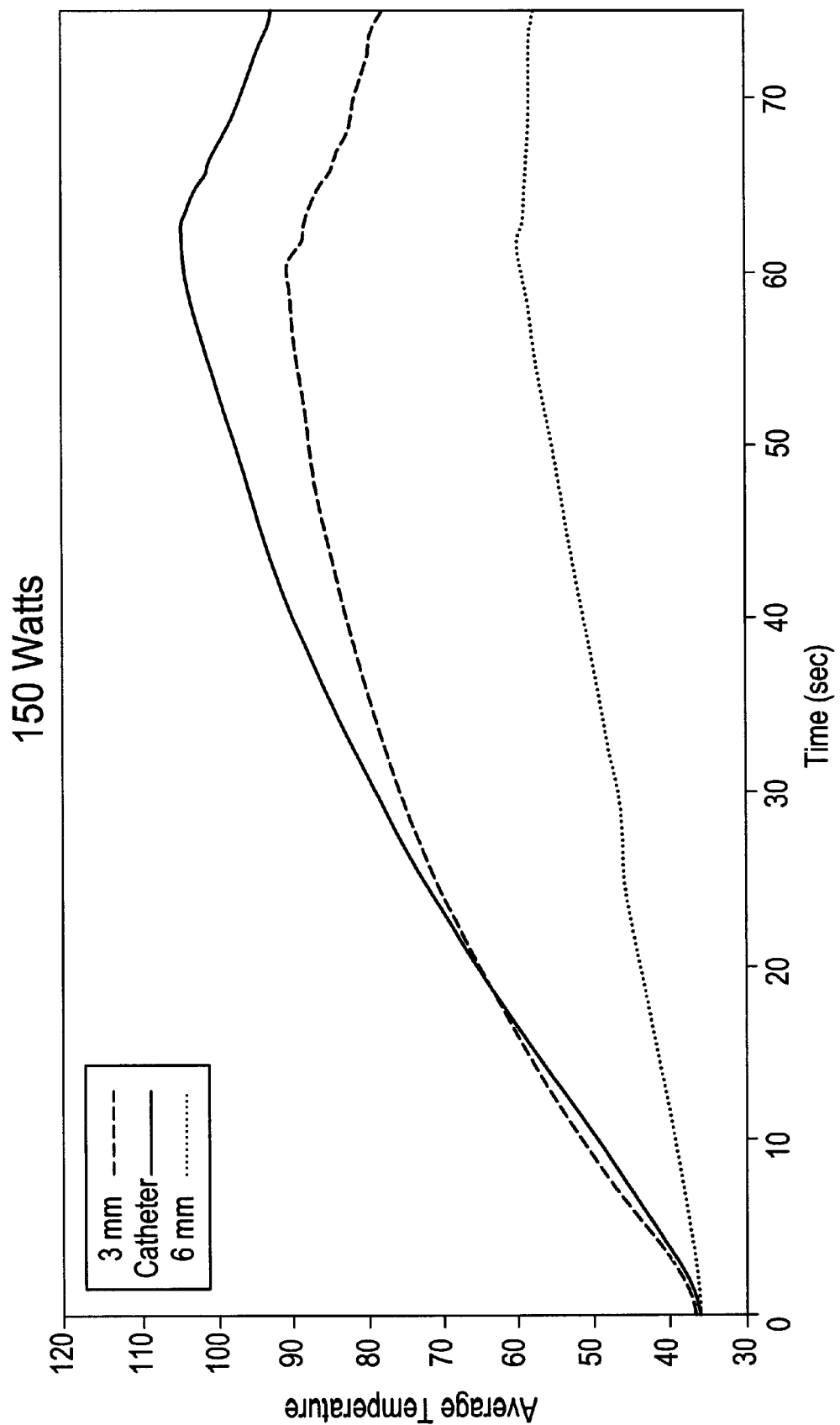
Figure 11A:
FIG. 11 are photographs of representative in vivo from thigh muscle model lesions produced with various applied power levels.
Figure 11B:
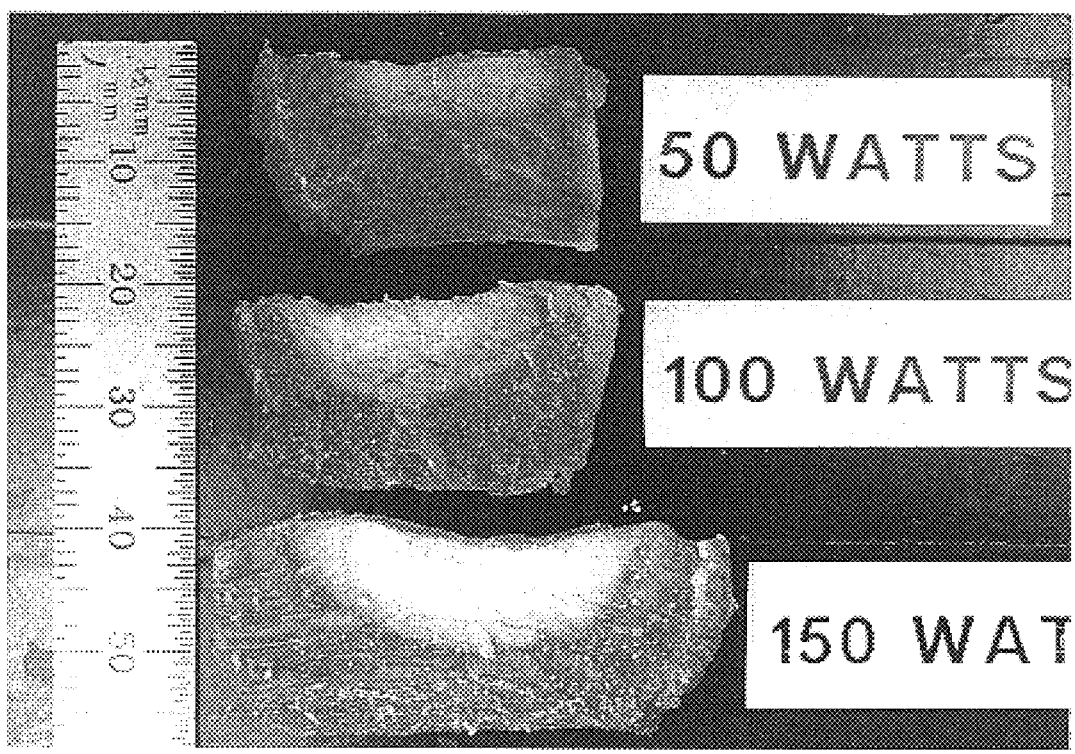

In the thigh muscle model, a total of 70 lesions were produced, 23 lesions created at 50 W, 24 lesions at 100 W, and 24 lesion at 150 W. For each power level, the peak and average temperatures declined as a function of depth. At 100 W the peak temperature declined from 78.7° C. at the antenna-tissue interface to 73.4° C. and 55.5° C. at 3 mm and 6 mm deep, respectively. The average temperature versus time course for the lesion formation is shown in FIG. 10. The peak and average temperatures increased significantly as a function of power. The peak surface temperature recorded at the antenna-tissue interface is as low as 65.9° C. at 50W and rises to 106.6° C. at 150W. Similar relationships were observed for the average temperatures. FIG. 11 shows the lesions produced with various applied powers. Note that although the measured power patterns of FIG. 5 indicate a ring of higher power, thermal conduction fills in the center of the ring to produce a convex lesion volume.

4. In Vivo Experiments on Open-Chest Pig Hearts

The experiment preparation for this animal test is similar to that described in the in vivo thigh muscle model experiment. Eight anesthetized pigs weighing between 70–90 kg were studied. A surface electrocardiogram was continually recorded during each procedure. A sternotomy incision was made to expose the heart and the pericardium was incised. The catheter was inserted into the left ventricle, and guided by fluoroscope, brought into contact with the left ventricle apex. Microwave power of 150 W was then delivered to the tissue for 60 s. After completion of the experiments, the pigs were sacrificed, the hearts were removed and the lesions were examined.

Figure 12:
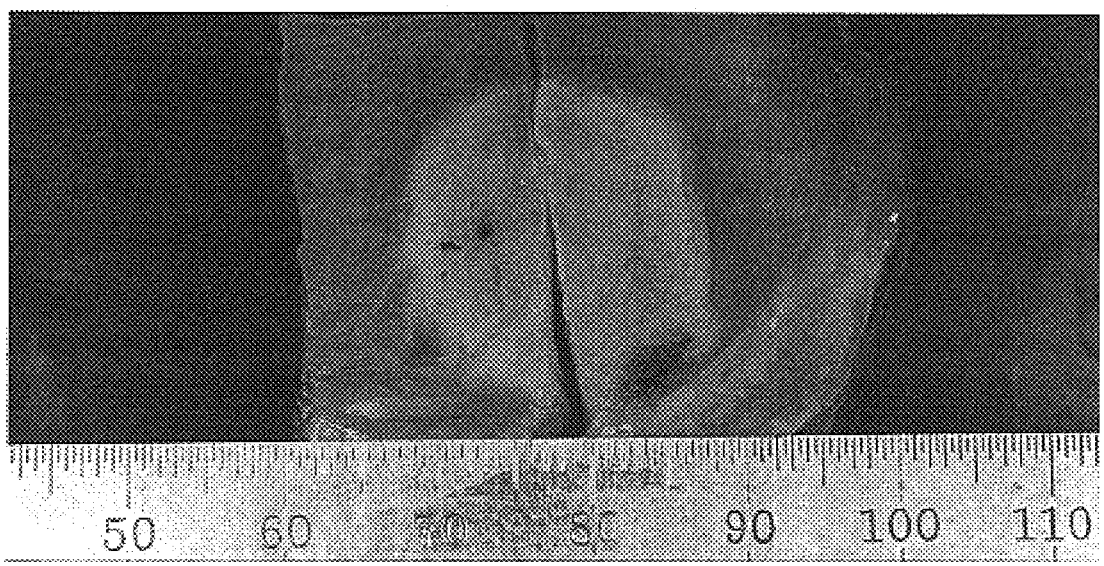
FIG. 12 is a photograph of a lesion generated by 60 s duration, 150 W power application, normal view, from the open-chest model.
Figure 13:
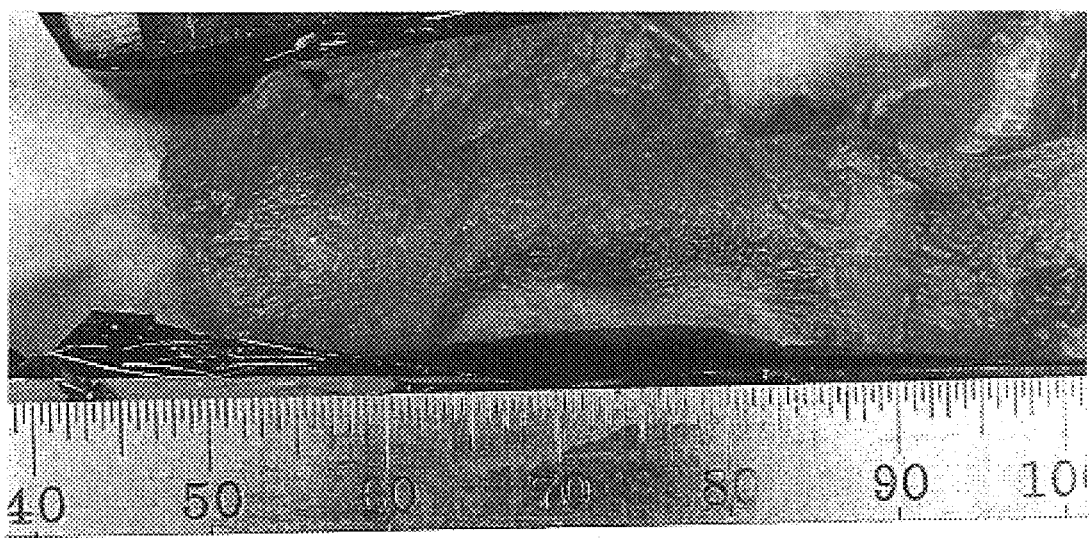
FIG. 13 is a photograph of a transmural lesion generated by 60 s duration, 150 W power application, depth view, from the open-chest model.

In the open-chest experiment, a total of 10 lesions were produced, with one or two lesions created on each pig. FIGS. 12 and 13 show the representative lesions. Note that the lesions are transmural and that there is no charring of surface tissue. The depths produced are sufficient for the ablation of an arrythomogenic focus that is very deep within the ventricular myocardium or is subepicardial.

The wide aperture spiral antenna effectively delivers power in cardiac tissue to create a wide, deep oblate spheroidal lesion. The spiral antenna is well matched to biological tissue at the operating frequency of 915 MHz. The antenna design is demonstrated in phantom tissue by measuring the reflection parameter $S_{11}$ and transmission parameter $S_{21}$, and by comparing them to a monopole antenna. Full power heating experiments at 50, 100, and 150 W on in vitro and in vivo animal tissue indicate that the field patterns in phantom combined with thermal conduction effects generate the desired lesion shape. These results show that the wide-aperture microwave spiral antenna design is capable of creating lesions of significant depth that may be applicable for the ablative therapy of ventricular tachycardia.

Alternative implementations may occur to those skilled in the field without departing from the spirit and true scope of the present invention. For example, the catheter may include steering mechanisms, and fluid cooling of the coaxial feed cable may be employed, as can mapping electrodes. Accordingly, the invention is not limited by what has been particularly shown and described.

REFERENCES

[1] Jackman, W., Wang, X., Friday, K., et al., "Catheter ablation of atrioventricular junction using radiofrequency current in 17 patients. Comparison of standard and large-tip electrode catheters," Circulation, 83:1562, 1991.

[2] Langberg, J., Chin M, Schcmp, D., et. al., "Ablation of atrioventricaular junction using radiofrequency energy using a new electrode catheter," Am J Cardiol, 67, pp. 142,1991.

[3] Rosen, A. and Rosen, H. (eds.), New Frontiers in Medical Device Technology, Wiley, New York, 1995.

[4] Morady, F., Harvey, M., Kalbfleisch, S., et. al., "Radiofrequency catheter ablation of ventricular tachycardia in patients with coronary artery disease," Circulation, 87, pp. 363–372, 1993.

[5] Kim, Y., Sosa-Suarez, G., Trouton, T., et. al., "Treatment of ventricular tachycardia by transcatheter radiofrequency ablation in patients with ischemic heart disease," Circulation, 89, pp. 1094–1102, 1994.

[6] Langberg, J., Wonnell, T., Chin, M., et. al., "Catheter Ablation or the Atrioventricular Junction Using a Helical Microwave Antenna: a Novel Means of Coupling Energy to the Endocardium," PACE, 14, pp. 2105–2133, 1991.

[7] Nevels, R., Dickey, G., Arndt, F., Raffoul, G., Carl, J., and Pacifico, A., "Microwave Catheter Design," IEEE Trans. Biomedical Engineering, 45, no. 7, July 1998.

[8] L. N. Horowitz, A. H. Harken, J. A. Kastar, and M. E. Josephson, "Ventricular resection guided by epicardial and endocardial mapping for treatment of recurrent ventricular tachycardia," N. Eng. J. Med., 302, p. 590, 1980.

[9] C. H. Durney, "Electromagnetic field propagation and interaction with tissues," in An Introduction to the Practical Aspects of Clinical Hyperthermia, S. B. Field and J. W. Hand, (Eds)., Taylor and Francis, New York, chap. 10, 1990.

[10] James G. Whayne, Sunil Nath, David E. Haines, "Microwave Catheter ablation of Myocardium in vitro, Assessment of the characteristics of tissue heating and injury," Circulation 89, no. 5, pp. 2390–2395, May 1994.

[11] Brian A. VanderBrink, Zeji Gu, Victor Rodriguez, Mark S. Link, Munther K. Homoud, N. A. Mark Estes III, Carey M. Rappaport, Paul J. Wang, "Microwave Ablation Using a Wide-aperture Antenna Design in a Porcine Thigh Muscle preparation: In vivo Assessment of Temperature Profile and Geometry," J. Cardiovascular Electrophysiology, February 2000. 9

[12] L. S. Taylor, "Electromagnetic syringe," IEEE Trans. Biomed. Eng., BME-25, pp. 303–304, May 1978.

[13] J. W. Strohbehn, E. W. Bowers, J. E. Walsh, and E. B. Douple, "An invasive antenna for locally induced hyperthermia for cancer therapy," J. Microwave Power, 14, pp. 339–350, 1979.

[14] T. Satoh and P. R. Stauffer, "Implantable helical coil microwave antenna for interstitial hyperthermia," Int. I. Hyperthermia, 4, no. 5, pp. 497–512, 1988.

[15] Tracy Wonnell, Paul Stauffer, and Jonathan Langberg, "Evaluation of Microwave and Radio Frequency Catheter Ablation in a Myocardium-Equivalent Phantom Model," IEEE Trans. Biomed. Eng., 39, no. 10, pp. 1086–1095, October 1992.

[16] Carey M Rappaport, Zeji Gu, Paul J Wang, "Wide-Aperture Microwave catheter-Based Cardiac ablation," Progress in Electromagnetics Research Symposium Digest, Hong Kong, p 316, January 1997.

[17] Zeji Gu, Carey M. Rappaport, Paul J, Wang, and Brian A. VanderBrink, "A 2¼ Turn Spiral Antenna for Catheter Cardiac Ablation," IEEE Trans. Biomed. Eng., 46, no. 12, pp. 1480–1482, December 1999.

[18] Guy, A. W., "Analysis of electromagnetic fields induced in biomedical tissues by thermographic studies on equivalent phantom models," IEEE Trans. Microwave Theory and Tech., 19, no. 2, pp. 205–214, February 1971.

[19] Nakagawa H, Yamanashi WS, et al, "Comparison of in vivo tissue temperature profile and lesion geometry for radiofrequency ablation with a saline-irrigated electrode versus temperature control in a canine thigh muscle preparation," Circulation, 91, pp. 2264–2273, 1995. 10

What is claimed is:

1. A cardiac ablation applicator comprising:

a catheter;

a coaxial cable disposed in the catheter and having an inner conductor and an outer conductor;

a spiral antenna connected to the inner conductor at an end of the coaxial cable;

a balloon enclosing the spiral antenna and coupled to the catheter to form a fluid tight enclosure; and an inflation tube disposed in the catheter for inflating and deflating the balloon;

the spiral antenna operative to be furled in a first elongated orientation inside the catheter for transluminal guiding of the catheter and capable of being unfurled from the catheter to a position outside of the catheter, and wherein the spiral antenna is operative to alter its orientation to a second deployed orientation, wherein the spiral antenna is configured and arranged at a position for microwave heating of surrounding tissue.

2. The cardiac ablation applicator of claim 1 wherein the spiral antenna is an extension of the inner conductor of the coaxial cable.

3. The cardiac ablation applicator of claim 1 wherein the spiral antenna is formed of a spring wire capable of being furled into generally linear form and unfurled into a spiral shape.

4. The cardiac ablation applicator of claim 1 including a low loss, low dielectric constant fluid within the balloon and surrounding the spiral antenna.

5. The cardiac ablation applicator of claim 4 wherein the fluid is air or nitrogen.

6. The cardiac ablation applicator of claim 4 wherein the fluid is a perfluorocarbon blood substitute.

7. A cardiac ablation applicator comprising:

a catheter;

an inflation tube disposed in the catheter;

a coaxial cable disposed in the catheter and having an inner conductor and an outer conductor and an insulation material disposed between the inner and outer conductors and an insulative cable jacket surrounding the outer conductor and disposed proximate to the confronting inner surface if the inflation tube;

a spiral antenna having an inner end connected to the inner conductor of the coaxial cable; and a balloon attached to an end of the catheter and enclosing the spiral antenna;

the coaxial cable being moveable to an inner position in the catheter to draw the spiral antenna into the catheter and cause furling of the spiral antenna into a first elongated orientation within the catheter;

the coaxial cable being moveable to an outer position in the catheter to position the spiral antenna outside of the catheter end, wherein the spiral antenna is operative to change its orientation from the first elongated orientation to a second deployed orientation in the balloon at which position the antenna is unfurled.

8. The cardiac ablation applicator of claim 7, wherein the spiral antenna is formed as one and one-quarter turns of wire.

9. The cardiac ablation applicator of claim 7 wherein the spiral antenna is operative at a frequency of about 915 MHz.

10. The cardiac ablation applicator of claim 9 wherein the spiral antenna is operative at a power in the range of about 50–150 watts.

* * * * *